(12) United States Patent
Sullivan

(10) Patent No.: US 6,444,835 B1
(45) Date of Patent: *Sep. 3, 2002

(54) TITANOCENE SYNTHESIS

(75) Inventor: Jeffrey M. Sullivan, Loveland, CO (US)

(73) Assignee: Boulder Scientific Co., Mead, CO (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/880,289

(22) Filed: Jun. 13, 2001

Related U.S. Application Data

(63) Continuation-in-part of application No. 09/784,736, filed on Feb. 15, 2001, now Pat. No. 6,307,063.

(51) Int. Cl.$^7$ ................................................ C07F 17/00
(52) U.S. Cl. ............................................ 556/54; 556/56
(58) Field of Search ..................................... 556/54, 56

(56) References Cited

U.S. PATENT DOCUMENTS

| | | | | | |
|---|---|---|---|---|---|
| 5,264,590 | A | * | 11/1993 | Strickler | 549/208 |
| 5,367,085 | A | * | 11/1994 | Strickler | 549/206 |
| 6,093,833 | A | * | 7/2000 | Kershner | 549/210 |
| 6,307,063 | B1 | * | 10/2001 | Sullivan | 549/208 |

* cited by examiner

*Primary Examiner*—Porfirio Nazario-Gonzalez
(74) *Attorney, Agent, or Firm*—Edward S. Irons

(57) ABSTRACT

A method for producing a titanocene wherein a $TiCl_3$ complex free from salts of metals other than titanium is reacted with a titanocene ligand.

4 Claims, No Drawings

TITANOCENE SYNTHESIS

This application is a continuation-in-part of application Ser. No. 09/784,736 filed Feb. 15, 2001 now U.S. Pat. No. 6,307,063.

FIELD OF THE INVENTION

This invention relates to titanium-trihalide complexes free from contamination with salts of metals other than titanium. More particularly, the invention relates to the synthesis of such adducts and to the conversion thereof to titanocenes.

BACKGROUND OF THE INVENTION

Application Ser. No. 09/784,736 describes a method for converting a Ti(IV) compound to a complex of a Ti(III) compound free of foreign metal contaminations. A preferred embodiment of the invention entails the reduction of $TiCl_4$ with particulate titanium in the presence of a reagent which forms a titanium trichloride complex insoluble in the reduction reaction mixture. According to that application, the consequent titanium trichloride complex may be converted to a titanocene in known manner. See, e.g., U.S. Pat. No. 6,218,557.

SUMMARY OF THE INVENTION

This invention provides methods for the conversion to titanocenes of the titanium trichloride complex as described in application Ser. No. 09/784,736.

DETAILED DESCRIPTION OF THE INVENTION

The invention may comprise a first step in which a titanium trichloride complex free of contamination with salts of other metals is produced. A second step of this invention may comprise treatment of a ligand with the titanium trichloride complex product of the first step to produce a titanocene.

EXAMPLE 1

One example illustrative of the first step is to charge a flask with particulate titanium (~100 mesh, 0.25 mole, 11.9 g) and dimethoxyethane (DME) (2 kg). With cooling slowly, add titanium tetrachloride (0.77 mole, 146.3 g), maintaining temperature at 0° C. After addition is complete, slowly warm to reflux, and hold at reflux for 8 hours. Cool to room temperature and filter. The cake comprises a $TiCl_3 \cdot DME$ complex which is free of contamination with any salt of a metal other than titanium. Dry the cake in vacua. Yield =246 g; 85%, based on total charge of titanium (both $TiCl_4$ and particulate titanium).

Analysis:
Ti=16.6%
Cl=36.6%
Theoretical:
Ti=16.5%
Cl=36.7%
Product is aluminum and magnesium free.

As explained in U. S. application Ser. No. 09/784,736, the reduction reaction may optionally be conducted in a medium comprising the complex-forming reagent per se or in such combination with any non-interfering medium. Suitable media include aliphatic and aromatic hydrocarbons; aromatic hydrocarbons are preferred.

Compounds which form a complex with Ti(III) compounds are known. See German patent application DE 197 39 946 A1 published Mar. 18, 1999. Each such complex-forming compound which yields a Ti(III) complex insoluble in the $TiCl_4$ reduction reaction mixture is useful in this invention. Preferred complex-forming compounds are ethers, typically tetrahydrofuran (THF) and DME.

Another aspect of the invention may include conversion of the Ti(III) complexes to metallocenes, which are also free of contamination with the salts of metals other than titanium, useful as olefin polymerization catalyst ligands, as olefin polymerization catalysts per se, or as components of olefin polymerization catalyst systems.

EXAMPLE 2

This example is a general illustration of the second step of the invention. The $TiCl_3 \cdot DME$ complex as produced in Example 1 is used instead of the $TiCl_3$ per se in each or any of the relevant examples of U.S. Pat. No. 6,218,557 to produce a titanocene.

I claim:

1. In a process for producing a titanocene wherein a titanium trichloride reagent is reacted with a ligand to produce a titanocene, the improvement which comprises utilizing as said titanium trichloride reagent, a titanium trichloride complex produced by treatment of titanium tetrachloride with particulate titanium in the presence of a reagent which forms a titanium trichloride complex
wherein a titanium trichloride complex free of contamination with a salt of a metal other than titanium is produced.

2. The process of claim 1 wherein said treating is conducted in a non-interfering medium in which said titanium trichloride complex is insoluble.

3. The process of claim 1 wherein said treatment is accomplished in a medium which forms a titanium chloride complex.

4. The process of claim 1 wherein said treatment is accomplished in a medium comprising dimethoxyethane or tetrahydrofuran.

* * * * *